Dec. 5, 1972 C. G. KLEHM Plant Pat. 3,266
PEONY PLANT
Filed Feb. 1, 1971
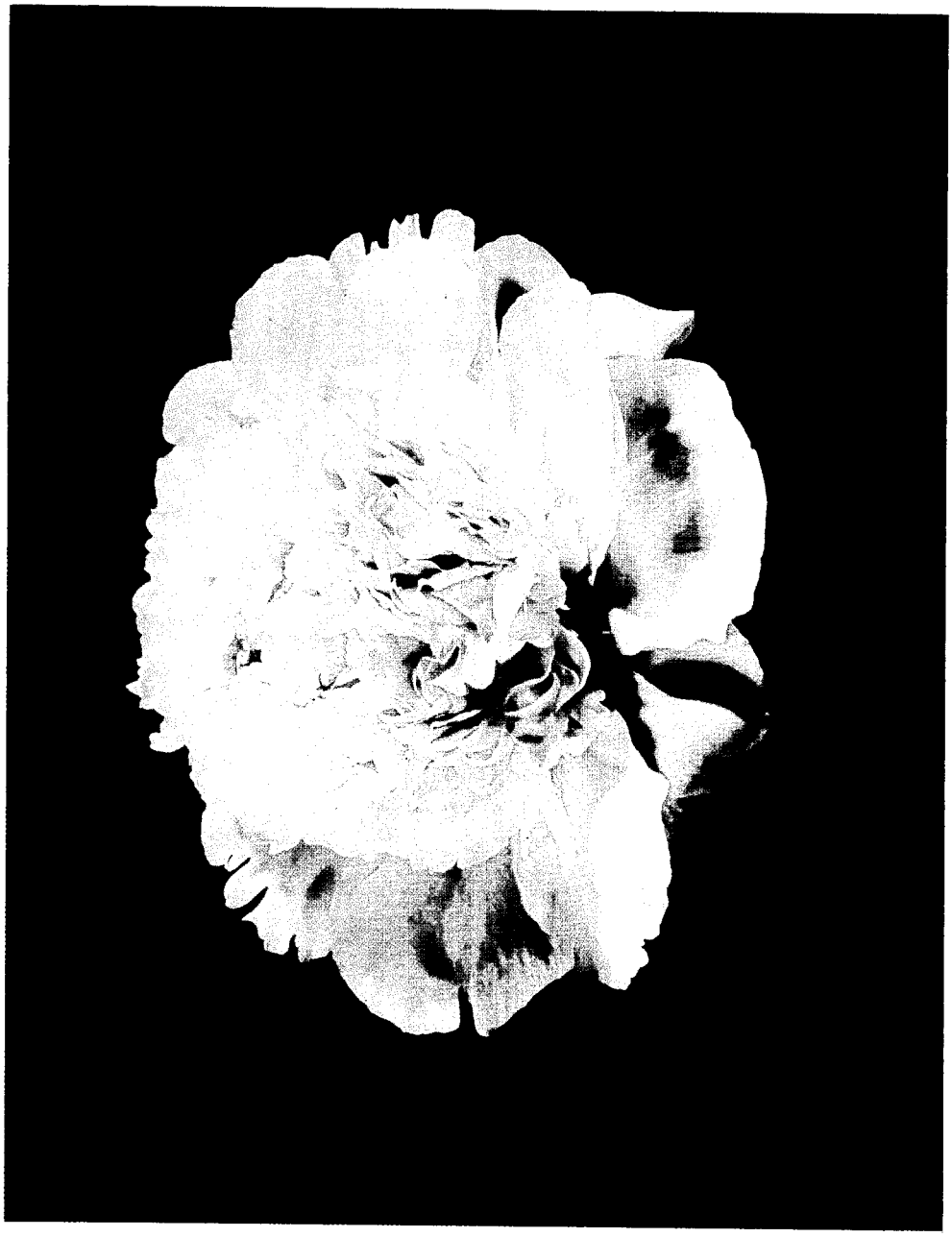
Inventor.
Carl G. Klehm
By: Robb & Robb
Attorneys.

United States Patent Office

Plant Pat. 3,266
Patented Dec. 5, 1972

3,266

PEONY PLANT

Carl G. Klehm, 2 E. Algonquin Road,
Arlington Heights, Ill. 60005

Filed Feb. 1, 1971, Ser. No. 111,775
Int. Cl. A01h 5/00
U.S. Cl. Plt.—68 1 Claim The present invention relates to a new and distinct variety of peony plant of the species botanically known as *Paeonia lactiflora,* which was originated by me by crossing an unnamed and unpatented "bull" type peony seedling, identified in my breeding records as No. 69J, with the peony variety known as "Mons. Jules Elie" (unpatented), the unnamed seedling being the male parent and "Mons. Jules Elie" being the female parent.

My new variety resulted from an extensive and prolonged program of breeding and testing conducted by me in an effort to produce new and improved or unique peony varieties, and was selected as one of many outstanding varieties resulting from this breeding program because of its unique combination of the following principal characteristics which distinguish the new variety from its parents, as well as from all other peony varieties in which I am aware:

(1) A relatively dwarf habit of growth ranging from about 20 inches to 24 inches tall, with short, stiff and weather-resistant stems;

(2) Clean and lush soft green foliage of attractive appearance;

(3) An extremely compact and bomb-shaped flower form;

(4) A distinctive and attractive cameo pink flower color, with red candy striping on the dorsal extremities of the topmost petals, and with a double row of guard petals which blend and mellow to a lighter and softer pink color at the petal extremities, while the extreme ventral petals in the bomb-shaped body of the flowers blend to a creamy peach color; and (5) A suitability for mass use in landscape hedges and background plantings, as well as for decorative cut arrangements.

Asexual reproduction of my new peony variety by root division, as performed by me in my nursery located at Arlington Heights, Ill., shows that the foregoing characteristics and distinction come true to form and are established and transmitted through succeeding propagations.

The accompanying drawing shows typical specimens of the vegetative growth and flowers of my new variety, as depicted in color as nearly true as it is reasonably possible to make the same in a color illustration of this character.

The following is a detailed description of the new variety, with color terminology in accordance with the Horticultural Colour Chart (1966 edition), published by the The Royal Horticultural Society, of London, England, as based on specimens grown and observed by me at Arlington Heights and Barrington, Ill.

Breeding: Seedling.
*Seed parent.*—"Mons. Jules Elie."
*Pollen parent.*—An unnamed seedling identified as No. 69J.

Propagation: Holds its distinguishing characteristics through succeeding propagations by root division.

FLOWER

Blooming habit: Annual.
Blooming season: Mid-season.
Bud:
*Size.*—Medium.
*Form.*—Smooth; round.
*Color.*—Shell pink, Fan 1, Plate 37D'.
*Sepals.*—Even edge. Color: Smooth green.
*Calyx.*—Polysepalous.
*Opening.*—Opens easily and dependably.
Bloom:
*Size.*—From medium small to medium (from about 5½ inches to 6 inches in diamter).
*Borne.*—Singly; usually one main bud per stem, with 2 or 3 auxiliary buds.
*Stems.*—Short (from 20 inches to 24 inches tall); strong.
*Form.*—Compact bomb-shaped.
*Petalage.*—Double.
*Color.*—Cameo pink, with red candy striping on the dorsal extremities of the topmost petals, and with a double row of guard petals which blend and mellow to a lighter and softer pink color at the petal extremities, while the extreme ventral petals blend to a creamy peach color; colors mainly correspond to Fan 1, Plates 49C and 49D.
*Variegations.*—None.
*Discolorations.*—None.
Petals:
*Texture.*—Medium thick.
*Appearance.*—Neat; glossy.
*Form.*—Slightly notched and slightly frilled.
*Arrangement.*—Imbricated.
*Persistence.*—Above average.
*Fragrance.*—None.
*Lasting qualities.*—Above average.

REPRODUCTIVE ORGANS

Stamens (male): None.
Stigmas (female): Few; immature.
Styles: Few; immature.
Fruit: None.

PLANT

Form: Short bush.
Growth: Rather dwarf; healthy; strong.
Foliage:
*Leaflets.*—5 or 6 in number.
*Size.*—Medium.
*Quantity.*—Medium.
*Color.*—Soft green, Fan 3, Plate 136C'.
*Shape.*—Elliptically acute.
*Texture.*—Smooth.
*Edge.*—Smooth.
*Serrations.*—None.
*Leaf Stem.*—Thick; succulent.
*Stipules.*—None.
*Disease resistance.*—Resistant to leaf blotch and other bacterial peony diseases, as determined by comparison with other varieties as grown at Arlington Heights and Barrington, Ill.

GENERAL OBSERVATIONS

The dwarf plant habit, attractive pink flower hues tipped with red candy striping, and compact bomb-shaped flower form, are distinctively unique in the Paeonia genus.

I claim:

1. A new and distinct variety of peony plant of the species botanically known as *Paeonia lactiflora,* substantially as herein shown and described, characterized particularly as to novelty by the unique combination of a relatively dwarf habit of growth ranging from about 20 inches to 24 inches tall, with short, stiff and weather-resistant stems, clean and lush soft green foliage of attractive appearance, an extremely compact and bomb-shaped flower form, a distinctive and attractive cameo pink flower color, with red candy striping on the dorsal extremities of the topmost petals, and with a double row of guard petals which blend and mellow to a lighter and softer pink color at the petal extremities, while the extreme central petals in the bomb-shaped body of the flower blend to a creamy peach color, and a suitability for mass use in landscape hedges and background plantings, as well as for decorative cut arrangements.

No references cited.

ROBERT E. BAGWILL, Primary Examiner